(12) United States Patent
Kim et al.

(10) Patent No.: US 8,766,015 B2
(45) Date of Patent: Jul. 1, 2014

(54) METHOD FOR PREPARING A GLYCOL MONO-TERTIARY-BUTYLETHER COMPOUND

(75) Inventors: Myeong-Seok Kim, Daejeon (KR); Jae-Hoon Uhm, Daejeon (KR); Min-Sup Park, Daejeon (KR); Hyoung-Jae Seo, Daejeon (KR); Kyoung-Tae Min, Daejeon (KR)

(73) Assignee: Daelim Industrial Co., Ltd., Jongno-Gu, Seoul (KR)

( * ) Notice: Subject to any disclaimer, the term of this patent is extended or adjusted under 35 U.S.C. 154(b) by 0 days.

(21) Appl. No.: 14/000,648

(22) PCT Filed: Feb. 21, 2012

(86) PCT No.: PCT/KR2012/001293
§ 371 (c)(1),
(2), (4) Date: Aug. 21, 2013

(87) PCT Pub. No.: WO2012/115422
PCT Pub. Date: Aug. 30, 2012

(65) Prior Publication Data
US 2013/0331613 A1    Dec. 12, 2013

(30) Foreign Application Priority Data

Feb. 22, 2011 (KR) .......................... 10-2011-0015415
Jun. 28, 2011 (KR) .......................... 10-2011-0062666

(51) Int. Cl.
*C07C 41/06* (2006.01)
(52) U.S. Cl.
USPC .......................................... 568/697; 568/619
(58) Field of Classification Search
None
See application file for complete search history.

(56) References Cited

U.S. PATENT DOCUMENTS

| 5,536,887 | A | * | 7/1996 | Minkkinen et al. | ........... 568/697 |
| 5,552,024 | A | | 9/1996 | Chang et al. | |
| 6,264,800 | B1 | | 7/2001 | Gupta | |

FOREIGN PATENT DOCUMENTS

| CN | 1065656 | 10/1992 |
| EP | 0530966 A2 | 3/1993 |
| JP | 59-051224 A | 3/1984 |
| KR | 10-2010-0097937 A | 9/2010 |
| KR | 10-2011-0094423 A | 8/2011 |

OTHER PUBLICATIONS

International Search Report for PCT/KR2012/001293 dated Aug. 29, 2012.

* cited by examiner

*Primary Examiner* — Brian J Davis
(74) *Attorney, Agent, or Firm* — Heslin Rothenberg Farley & Mesiti P.C.

(57) ABSTRACT

Disclosed is a method of preparing a glycol mono-tertiary-butyl ether compound using a $C_4$ hydrocarbon mixture containing isobutene and a glycol compound as reactants, in which a glycol di-tertiary-butyl ether compound as a byproduct is decomposed into isobutene and a glycol compound and the obtained isobutene and glycol compound are recycled as reactants, whereby product yield per unit raw material may be maximized. The method includes a catalytic reaction step for preparing a glycol mono-tertiary-butyl ether compound and a glycol di-tertiary-butyl ether compound as a byproduct by reaction between a glycol compound and a $C_4$ hydrocarbon mixture containing isobutene in the presence of an acidic catalyst, a byproduct extraction step for separating the glycol mono-tertiary-butyl ether compound and the glycol di-tertiary-butyl ether compound, prepared through the catalytic reaction step, using a hydrophilic extractant and a lipophilic extractant, and a byproduct decomposition and recycling step for decomposing the separated glycol di-tertiary-butyl ether compound into a glycol compound and isobutene and recycling the decomposed glycol compound and isobutene as the reactants to the catalytic reaction step.

6 Claims, 1 Drawing Sheet

METHOD FOR PREPARING A GLYCOL MONO-TERTIARY-BUTYLETHER COMPOUND

CROSS REFERENCE TO RELATED APPLICATIONS

This application is a national stage filing under section 371 of International Application No. PCT/KR2012/001293 filed Feb. 21, 2012 and published as WO 2012/115422, and claims priority to Korean Patent Application No. 10-2011-0015415 filed on Feb. 22, 2011, and Korean Patent Application No. 10-2011-0062666 filed on Jun. 28, 2011, the entire disclosure of these applications being hereby incorporated herein by reference.

TECHNICAL FIELD

The present invention relates to a method of preparing a glycol mono-tertiary-butyl ether compound, and more particularly to a method of preparing a glycol mono-tertiary-butyl ether compound using a $C_4$ hydrocarbon mixture containing isobutene and a glycol compound as reactants, in which a glycol di-tertiary-butyl ether compound as a byproduct is decomposed into isobutene and a glycol compound and the obtained isobutene and glycol compound are recycled as reactants, whereby product yield per unit raw material may be maximized.

BACKGROUND ART

Glycol mono-tertiary-butyl ether compounds are materials that can replace glycol mono-butyl ether compounds, which are components of stripping solutions used to strip resist from a substrate in a process of manufacturing a semiconductor device, a liquid crystal display device, or the like. In addition, glycol mono-tertiary-butyl ether compounds may be used as a high boiling point solvent to provide leveling effects, in fields such as paints, coatings, and the like.

Glycol mono-butyl ether compounds are generally prepared by the reaction of butyl alcohol and ethylene oxide in the presence of sodium ethoxide as a catalyst. However, butyl alcohol and ethylene oxide as raw materials are relatively high in cost, and the catalyst is also expensive, must be used in large amounts, has a risk of explosion, and requires high temperature and high pressure reaction conditions.

Thus, methods of synthesizing glycol mono-tertiary-butyl ether compounds by reacting glycol compounds and butane-based compounds such as isobutene and the like in the presence of acidic catalysts have recently been used. Chinese Patent Application No. 1065656 discloses a method of synthesizing diethylene glycol mono-tertiary-butyl ether by reaction between diethylene glycol and isobutene. However, mixability of ethylene glycol and the butane-based compound in the reaction is so poor that the reaction does not effectively occur. In addition, yield of diethylene glycol di-tertiary-butyl ether as a byproduct is between about 15% and about 30% and thus yield of diethylene glycol mono-tertiary-butyl ether is reduced.

DISCLOSURE

Technical Problem

Therefore, the present invention has been made in view of the above problems, and it is an object of the present invention to provide a method of preparing a glycol mono-tertiary-butyl ether compound by decomposing a glycol di-tertiary-butyl ether compound as a byproduct and recycling the obtained compounds as reactants, whereby yield of the glycol mono-tertiary-butyl ether compound may be maximized and manufacturing costs may be minimized.

Technical Solution

In accordance with an aspect of the present invention, the above and other objects can be accomplished by the provision of a method of preparing a glycol mono-tertiary-butyl ether compound, the method including a catalytic reaction step for preparing a glycol mono-tertiary-butyl ether compound and a glycol di-tertiary-butyl ether compound as a byproduct by reaction between a glycol compound and a $C_4$ hydrocarbon mixture containing isobutene in the presence of an acidic catalyst, a byproduct extraction step for separating the glycol mono-tertiary-butyl ether compound and the glycol di-tertiary-butyl ether compound, prepared in the catalytic reaction step, using a hydrophilic extractant and a lipophilic extractant, and a byproduct decomposition and recycling step for decomposing the separated glycol di-tertiary-butyl ether compound into a glycol compound and isobutene and recycling the decomposed glycol compound and isobutene as the reactants to the catalytic reaction step.

Advantageous Effects

A method of preparing a glycol mono-tertiary-butyl ether compound, according to the present invention, is easily used and relatively safe and uses inexpensive raw materials (a $C_4$ hydrocarbon mixture containing isobutene and a glycol compound), and thus, the preparation process may be convenient and a product may be obtained at low cost. In addition, reaction may be performed under relatively non-stringent conditions. Moreover, a glycol di-tertiary-butyl ether compound as a byproduct may be completely decomposed into the isobutene and glycol compound that are reactants and reused as raw materials, whereby raw material costs may be reduced, yield of the glycol mono-tertiary-butyl ether compound may be maximized, and costs for byproduct treatment may be decreased.

DESCRIPTION OF DRAWINGS

The above and other objects, features and other advantages of the present invention will be more clearly understood from the following detailed description taken in conjunction with the accompanying drawings, in which.

DETAILED DESCRIPTION

Hereinafter, the present invention will be described in detail with reference to the accompanying drawings.

Figure 1:
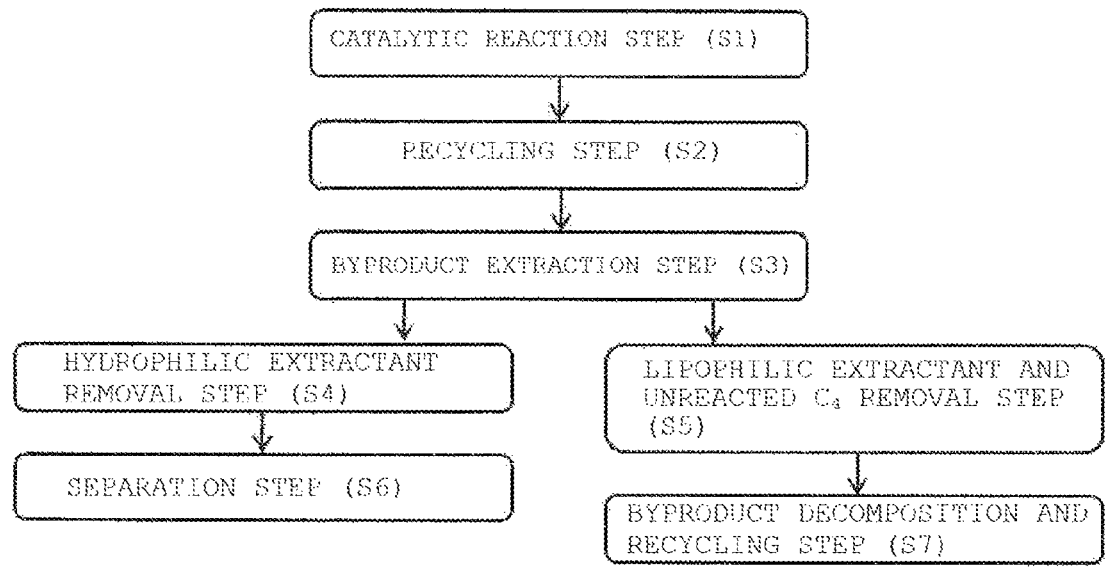
FIG. 1 is a flowchart illustrating a method of preparing glycol mono-tertiary-butyl ether, according to an embodiment of the present invention.

FIG. 1 is a flowchart illustrating a method of preparing glycol mono-tertiary-butyl ether, according to an embodiment of the present invention. As illustrated in FIG. 1, the method of preparing glycol mono-tertiary-butyl ether according to the present invention may include a catalytic reaction step (step S1), a byproduct extraction step (step S3), and a byproduct decomposition and recycling step (step S7), whereby product yield per unit raw material may be maximized. In addition, the method may further include a recycling step (step S2), a hydrophilic extractant removal step (step S4), a lipophilic extractant and unreacted C4 removal step (step S5), and a separation step (step S6).

Figure 2:
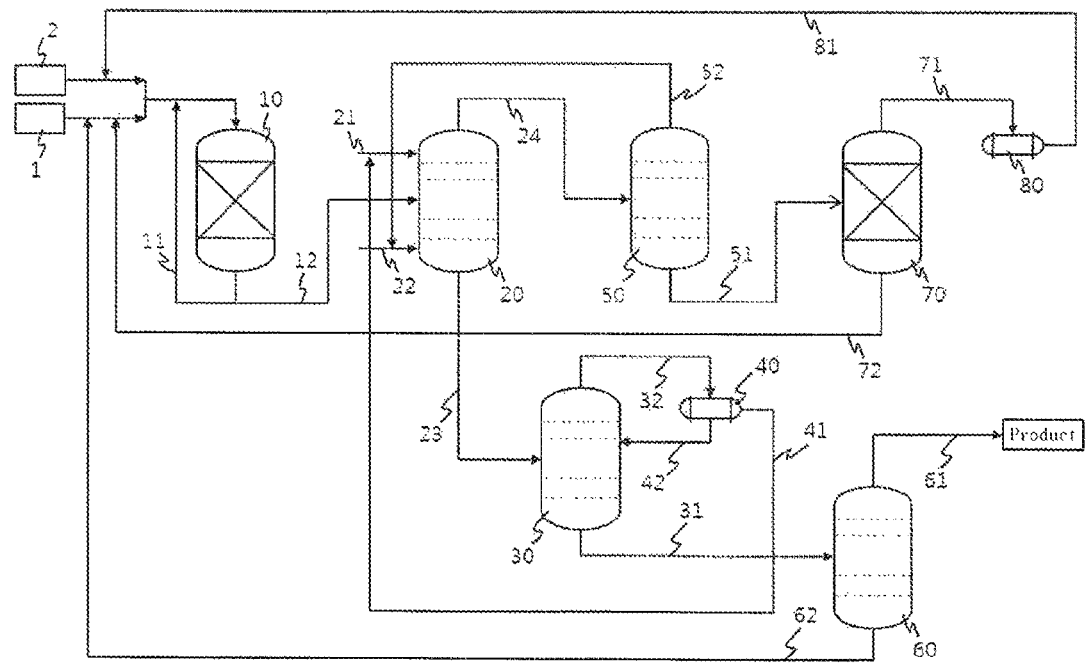
FIG. 2 is a schematic view for explaining the method of preparing glycol mono-tertiary-butyl ether illustrated in FIG. 1.

FIG. 2 is a schematic view for explaining the method of preparing glycol mono-tertiary-butyl ether illustrated in FIG. 1 and illustrates devices used in the preparation method and flow lines. As illustrated in FIGS. 1 and 2, the catalytic reaction step (step S1) involves preparing a glycol mono-tertiary-butyl ether compound and a glycol di-tertiary-butyl ether compound as a byproduct by introducing, as reactants, a glycol compound 1 and a $C_4$ hydrocarbon (hydrocarbon with four carbon atoms) mixture 2 containing isobutene into a catalytic reactor 10 in the presence of an acidic catalyst, in particular a general tubular reactor packed with an acidic catalyst so that the acidic catalyst does not escape from the reactor to induce reaction between the reactants.

A general glycol compound may be used as the glycol compound 1. Preferably, the glycol compound 1 may be a glycol compound represented by Formula 1 below and, more preferably, may be diethylene glycol (i.e., a glycol compound of Formula 1, wherein $R_1$ and $R_2$ are each independently a hydrogen atom and n is 1):

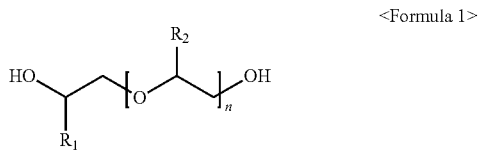

<Formula 1> wherein $R_1$ and $R_2$ are each independently a hydrogen atom or a $C_1$-$C_5$ alkyl group, and n is an integer of 0 to 4.

The $C_4$ hydrocarbon mixture 2 containing isobutene is a $C_4$ hydrocarbon mixture containing 10 wt % or more, preferably 30 wt % or more of isobutene, and examples thereof include, but are not limited to, a $C_4$ fraction generated through catalytic cracking of heavy oil in a petroleum refining process, $C_4$ raffinate generated through naphtha pyrolysis, isobutene, and mixtures thereof. When the amount of isobutene in the $C_4$ hydrocarbon mixture 2 is less than 10 wt %, yield of the glycol mono-tertiary-butyl ether compound may be reduced and reaction efficiency may be decreased.

The glycol compound 1 and isobutene contained in the $C_4$ hydrocarbon mixture 2 may be introduced in a molar ratio of 1:1 to 5:1, preferably 1.5:1 to 3:1 (glycol compound: isobutene). When the molar ratio of the glycol compound to isobutene is less than 1:1, reaction efficiency of the catalytic reaction step may be too low. On the other hand, when the molar ratio of the glycol compound to isobutene exceeds 5:1, the amount of unreacted glycol compound increases, and thus, manufacturing costs for recycling the unreacted glycol compound increase, resulting in increased raw material costs.

The acidic catalyst may be a general acid catalyst, for example, a strongly acidic cation exchange resin. Preferably, a strongly acidic cation exchange resin, which is insoluble in water and has a sulfonic acid group ($SO_3H$) may be used. In particular, examples of strongly acidic cation exchange resins include, but are not limited to, a styrene-sulfonic acid type cation exchange resin, a phenol-sulfonic acid type cation exchange resin, cross-linked conjugates thereof, sulfonated coal, and sulfonated asphalt.

A reaction temperature of the catalytic reaction step is between 30° C. and 90° C., preferably between 45° C. and 65° C. When the reaction temperature is less than 30° C., reaction rate becomes slow and thus reaction efficiency may be reduced. On the other hand, when the reaction temperature exceeds 90° C., a large amount of byproducts are produced due to side reaction and the reaction catalyst may be broken or deformed. In addition, a pressure of the catalytic reaction step may be arbitrarily adjusted according to reaction temperature, and the catalytic reaction step may be performed at a pressure at which the $C_4$ hydrocarbon mixture containing isobutene is in liquid phase. More preferably, the catalytic reaction step may be performed at a pressure of 5 to 10 atm. When the catalytic reaction step is performed within the above-described pressure range, yield and efficiency of the catalytic reaction increase. In addition, in the catalytic reaction step, the reactants 1 and 2 may be introduced at a weight hourly space velocity (WHSV) of 0.1 to 10, preferably 0.5 to 3. When the WHSV is less than 0.1, production efficiency may be reduced. On the other hand, when the WHSV exceeds 10, reaction efficiency may be decreased.

When the glycol compound of Formula 1 is used in the catalytic reaction, the produced glycol mono-tertiary butyl ether may be represented by Formula 2 below, and the produced glycol di-tertiary butyl ether may be represented by Formula 3 below:

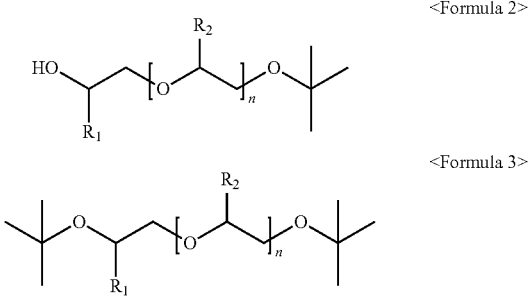

<Formula 2>

<Formula 3> wherein, in Formulas 2 and 3, $R_1$, $R_2$, and n are the same as defined in Formula 1 above.

The recycling step (step S2) involves partially recycling the reaction mixture (reaction products, i.e., the glycol mono-tertiary-butyl ether compound and the glycol di-tertiary-butyl ether compound) of the catalytic reaction step (step S1) and unreacted reactants (i.e., an unreacted glycol compound and an unreacted $C_4$ hydrocarbon mixture) and then mixing the same with the reactants 1 and 2, followed by repeating the catalytic reaction step (step S1). In general, the raw materials (reactants) of the catalytic reaction, i.e., the glycol compound 1 and the $C_4$ hydrocarbon mixture 2 containing isobutene, do not readily mix, and thus, the catalytic reaction does not proceed smoothly. When the reaction mixture is partially recycled, however, the glycol mono-tertiary-butyl ether compound included in the reaction mixture accelerates mixing of the glycol compound 1 and the $C_4$ hydrocarbon mixture 2 containing isobutene, which enables the reaction to proceed smoothly. In particular, in the recycling step (step S2), a portion of the reaction mixture having passing through the catalytic reactor 10 may be mixed with the reactants 1 and 2 via a first circulation tube 11 and then reintroduced into the catalytic reactor 10, while the remaining portion thereof may be transferred to an extraction column 20 via a product transfer tube 12. The amount of the recycled reaction mixture 11 of the catalytic reaction step (step S1) may be 1 to 20 times (weight ratio) that of a non-recycled reaction mixture 12. When the amount of the recycled reaction mixture 11 is less than 1 times that of the non-recycled reaction mixture 12, the reactants 1 and 2 do not readily mix and thus the reaction is not smoothly performed. On the other hand, when the amount of the recycled reaction mixture 11 exceeds 20 times that of the non-recycled reaction mixture 12, the amount of byproducts increases and thus production efficiency may be reduced.

The byproduct extraction step (step S3) involves separating the glycol mono-tertiary-butyl ether compound and the glycol di-tertiary-butyl ether compound as a byproduct, prepared in the catalytic reaction step (step S1), using a hydrophilic extractant and a lipophilic extractant. The hydrophilic extractant may be a hydrophilic extractant capable of forming a hydrophilic compound layer (a water layer 23) by extracting, from the reaction mixture, a hydrophilic compound such as the glycol mono-tertiary-butyl ether compound or the like, e.g., a general hydrophilic extractant. Examples of general hydrophilic extractants include, but are not limited to, $C_1$-$C_8$ alcohols, $C_2$-$C_{10}$ glycols, and mixtures thereof. Examples of $C_1$-$C_8$ alcohols include, but are not limited to, methanol, ethanol, propanol, pentanol, and hexanol. Example of $C_2$-$C_{10}$ glycols include, but are not limited to, ethylene glycol, propylene glycol, diethylene glycol, and dipropylene glycol. In addition, the lipophilic extractant may be a lipophilic extractant capable of forming a lipophilic compound layer (an organic layer 24) by extracting, from the reaction mixture, a lipophilic compound such as the glycol di-tertiary-butyl ether compound or the like, e.g., a general lipophilic extractant. For example, a $C_2$-$C_{16}$ hydrocarbon, preferably a $C_4$ hydrocarbon compound that is the same as the $C_4$ hydrocarbon mixture 2 may be used as the lipophilic extractant.

In the byproduct extraction step (step S3), for example, the reaction products (the reaction mixture) prepared in the catalytic reaction step (step S1) are transferred via the product transfer tube 12 and introduced into the extraction column 20, which is a multistep extraction column. Simultaneously, the hydrophilic extractant (e.g., water or the like) is introduced into an upper part of the extraction column 20 via a hydrophilic extractant transfer tube 21 and the lipophilic extractant (e.g., $C_4$ hydrocarbon or the like) is introduced into a lower part of the extraction column 20 via a lipophilic extractant transfer tube 22. Next, the introduced hydrophilic extractant is transferred to a bottom part of the extraction column 20 from the upper part thereof, is discharged in the form of the hydrophilic compound layer 23 from the bottom part of the extraction column 20, together with the glycol mono-tertiary-butyl ether compound as a main reaction product and the unreacted glycol compound, and then is transferred to a hydrophilic extractant stripper 30. The introduced lipophilic extractant moves to a top part of the extraction column 20 from the lower part thereof, is discharged in the form of the lipophilic compound layer 24 from the top part of the extraction column 20, together with the glycol di-tertiary-butyl ether compound as a byproduct and the unreacted $C_4$ hydrocarbon mixture, and then is transferred to a lipophilic extractant stripper 50. Through these processes, the glycol mono-tertiary-butyl ether compound and the glycol di-tertiary-butyl ether compound are separated.

As the extraction column 20, a general multistep (e.g., two to thirty step) extraction column, for example, a countercurrent multistep liquid-liquid extraction device or the like may be used, and type of the extraction column 20 may vary according to a pressure of the catalytic reactor 10. In particular, the extraction column 20 operates at a temperature ranging from 10° C. to 60° C., preferably from 20° C. to 40° C. and at a pressure of normal pressure (1 atm) to 15 bar, preferably between 1 atm and 12 bar, and more preferably between 2 bar and 10 bar. When the operating temperature of the extraction column 20 is less than 10° C., energy waste occurs due to addition of a refrigerant. On the other hand, when the operating temperature of the extraction column 20 exceeds 60° C., raw material costs increase because of energy input due to supply of a heat source. When the operating pressure of the extraction column 20 is less than 1 atm, plant equipment is needed for pressure reduction. On the other hand, when the operating pressure of the extraction column 20 exceeds 15 bar, expensive materials corresponding thereto need to be used. The extraction column 20 and separation of the glycol mono-tertiary-butyl ether compound and the glycol di-tertiary-butyl ether compound are disclosed in more detail in Korean Patent Application No. 10-2010-0056083, the disclosure of which is incorporated herein by reference.

The hydrophilic extractant removal step (step S4) involves removing (separating) the hydrophilic extractant from the hydrophilic compound layer 23 discharged from the bottom part of the extraction column 20. For example, the hydrophilic extractant, the glycol mono-tertiary-butyl ether compound, and the unreacted glycol compound may be separated by distilling the hydrophilic compound layer 23 using the hydrophilic extractant stripper 30 in the form of a multistep (five to fifty step) distillation column. In this regard, upon passing the hydrophilic compound layer 23 through the hydrophilic extractant stripper 30, the hydrophilic extractant is discharged via an upper connection tube 32 of the hydrophilic extractant stripper 30 and is captured by a condensing drum 40. Simultaneously, the glycol mono-tertiary-butyl ether compound as a main product and the unreacted glycol compound are discharged via a lower connection tube 31 of the hydrophilic extractant stripper 30 and transferred to a glycol mono-tertiary-butyl ether distillation column 60. The captured hydrophilic extractant may be recycled (via a hydrophilic extractant recycling stream 41) to the extraction column 20 via the hydrophilic extractant transfer tube 21 or may be reintroduced into the hydrophilic extractant stripper 30 via a hydrophilic extractant reintroduction stream 42.

In this regard, a temperature at an upper portion (top part) of the hydrophilic extractant stripper 30 is a boiling point of the hydrophilic extractant under given pressure conditions. For example, when water is used alone as the hydrophilic extractant and the operating pressure of the extraction column 20 is 0.1 bar and 1 atm, the temperatures at the top part of the hydrophilic extractant stripper 30 are about 45° C. and 100° C., respectively. In addition, a temperature at a lower portion (bottom part) of the hydrophilic extractant stripper 30 is a boiling point of a mixture of glycol mono-tertiary-butyl ether and the unreacted glycol compound under given pressure conditions.

The lipophilic extractant and unreacted $C_4$ (unreacted $C_4$ hydrocarbon mixture) removal step (step S5) involves removing (separating) the unreacted $C_4$ hydrocarbon mixture and the lipophilic extractant (e.g., $C_4$ hydrocarbon) from the lipophilic compound layer 24 discharged from the top part of the extraction column 20. The separation process may be performed using various methods known in the art. For example, the lipophilic extractant, the unreacted $C_4$ (unreacted $C_4$ hydrocarbon mixture), and the glycol di-tertiary-butyl ether compound may be separated by distilling the lipophilic compound layer 24 using a $C_4$ stripper 50 in the form of a multistep (five to fifty steps) distillation column. In this regard, upon passing the lipophilic compound layer 24 through the $C_4$ stripper 50, the glycol di-tertiary-butyl ether compound is discharged via a lower connection tube 51 of the $C_4$ stripper 50 and transferred to a decomposition reactor 70. Simultaneously, the lipophilic extractant and the unreacted $C_4$ hydrocarbon mixture may be discharged via an upper connection tube 52 of the C₄ stripper 50 and recycled (via a lipophilic extractant recycling stream 52) to the extraction column 20 via the lipophilic extractant transfer tube 22.

In this regard, an operating pressure of the C₄ stripper 50 may vary according to kind of the lipophilic extractant. For example, when an extractant having 4 carbon atoms or less is used, the C₄ stripper 50 operates at a pressure of about 4 bar. In addition, when an extractant having 5 to 8 carbon atoms is used, the C₄ stripper 50 operates at 1 atm. In addition, when an extractant having 9 carbon atoms or more is used, the C₄ stripper 50 may operate by vacuum distillation. A temperature at an upper portion (top part) of the C₄ stripper 50 is a boiling point of a mixture of the lipophilic extractant and the unreacted C₄ hydrocarbon mixture under given pressure conditions at the top part thereof, and a temperature at a lower portion (bottom part) of the C₄ stripper 50 is a boiling point of glycol di-tertiary-butyl ether under given pressure conditions (e.g., 1 atm to 2 bar) at the bottom part thereof.

The separation step (step S6) involves purifying the glycol mono-tertiary-butyl ether compound as a main product. For example, the glycol mono-tertiary-butyl ether compound and the unreacted glycol compound may be separated and purified by distilling the glycol mono-tertiary-butyl ether compound and the unreacted glycol compound that are discharged via the lower connection tube 31 of the hydrophilic extractant stripper 30 using the glycol mono-tertiary-butyl ether distillation column 60 in the form of a multistep (5 to 50 step) distillation column. In this regard, upon passing the glycol mono-tertiary-butyl ether compound and the unreacted glycol compound through the distillation column 60, the glycol mono-tertiary-butyl ether compound may be discharged via an upper connection tube 61 of the distillation column 60 and, simultaneously, the unreacted glycol compound may be discharged via a lower connection tube 62 of the distillation column 60 and reintroduced into the catalytic reactor 10 together with the glycol compound 1.

In this regard, the distillation column 60 operates at a pressure between 0.05 bar and 1 atm, preferably between 0.05 and 0.5 bar, and more preferably between 0.08 bar and 0.2 bar. A temperature at an upper portion (top part) of the distillation column 60 is a boiling point of glycol mono-tertiary-butyl ether under given pressure conditions, and a temperature at a lower portion (bottom part) of the distillation column 60 is a boiling point of the unreacted glycol compound under given pressure conditions. When the operating pressure of the distillation column 60 is less than 0.05 bar, expensive equipment and facility investment costs for adjustment of the pressure are needed, thus being uneconomical. On the other hand, when the operating pressure of the distillation column 60 exceeds 1 atm, energy may be wasted.

The byproduct decomposition and recycling step (step S7) involves decomposing the glycol di-tertiary-butyl ether compound as a byproduct generated by the catalytic reaction into isobutene and a glycol compound and to recycle the obtained compounds as reactants, to maximize product yield (a glycol mono-tertiary-butyl ether compound) per unit raw material. For example, the glycol di-tertiary-butyl ether compound discharged via the lower connection tube 51 of the C₄ stripper 50 is introduced into the decomposition reactor 70 of a fixed bed type in which a general tubular reactor is packed with an acid catalyst so that the acid catalyst does not escape therefrom and is decomposed into a glycol compound and isobutene at a temperature between 40° C. and 250° C., preferably between 60° C. and 180° C., and the obtained glycol compound and isobutene are recycled (reintroduced) into the catalytic reactor 10. The isobutene may be discharged via an upper (top) connection tube 71 of the decomposition reactor 70, be captured by an isobutene condensing drum 80, be recycled via an isobutene recycling stream 81, and then be introduced into the catalytic reactor 10 together with the C₄ hydrocarbon mixture 2 containing isobutene. The regenerated glycol compound may be discharged via a lower (bottom) connection tube 72 of the decomposition reactor 70 and then introduced into the catalytic reactor 10 together with the glycol compound 1. Through inclusion of the byproduct decomposition and recycling step (step S7), an ideal reactor (reaction processes) with little loss of introduced raw materials (i.e., the glycol compound 1 and the C₄ hydrocarbon mixture 2) may be configured.

The acid catalyst used in the decomposition reactor 70 may be a general acid catalyst used in the catalytic reactor 10. Examples of acid catalysts include, but are not limited to, a strongly acidic clay catalyst, silica, alumina, zeolite, molybdenum oxide, and a strongly acidic cation exchange resin. Preferably, the acid catalyst is a strongly acidic clay catalyst.

In the byproduct decomposition and recycling step (step S7), when the decomposition reaction temperature is less than 40° C., a rate of the decomposition reaction decreases and thus reaction efficiency may be reduced. On the other hand, when the decomposition reaction temperature exceeds 250° C., the amount of byproducts may increase due to condensation reaction of the glycol compound and the reaction catalyst may be broken or deformed. In addition, the decomposition reaction pressure may be arbitrarily adjusted by one skilled in the art. For example, the decomposition reaction may be performed at a pressure between 1 atm and 10 atm, preferably between 1 and 5 atm. When the decomposition reaction pressure is within the above-described range, decomposition reaction efficiency increases. In addition, in the decomposition reaction, the byproduct may be introduced into the decomposition reactor 70 at a weight hourly space velocity (WHSV) of 0.1 to 20, preferably between 0.5 and 10. When the WHSV is less than 0.1, decomposition production efficiency may be reduced. On the other hand, when the WHSV exceeds 20, decomposition reaction efficiency may be reduced.

MODE FOR INVENTION

Hereinafter, the present invention will be described more fully with reference to the following examples. These examples are provided for illustrative purposes only and should not be construed as limiting the scope and spirit of the present invention.

EXAMPLES 1 TO 8 AND COMPARATIVE EXAMPLES 1 TO 3

Preparation of Diethylene Glycol Mono-Tertiary-Butyl Ether

As the catalytic reactor 10 illustrated in FIG. 2, a double tube type reactor having a length of 60 cm and an inner tube diameter of ½ inches, packed with 50 g of a strongly acidic cation exchange resin (Amberlite catalyst composed of a microporous sulfonated divinylbenzene-cross-linked polystyrene resin), was used. As the decomposition reactor 70 illustrated in FIG. 2, a double tube type decomposition reactor having a length of 60 cm and an inner tube diameter of ½ inches, packed with 50 g of a strongly acidic clay catalyst, was used. To control reaction heat of each of the reactors 10 and 70, cooling water was circulated via an outer tube of the catalytic reactor 10 or heat transfer oil was circulated via an outer tube of the decomposition reactor 70. In addition, 15-step distillation columns were used as the extraction column 20, the hydrophilic extractant stripper 30, the C₄ stripper 50, and the glycol mono-tertiary-butyl ether distillation column 60. In addition, diethylene glycol (DEG) was used as the glycol compound 1, and C₄ hydrocarbon mixtures having the compositions shown in Table 1 below were used as the C₄ hydrocarbon mixture 2 containing isobutene (IB). The raw materials, i.e., the reactants 1 and 2, were transferred using a mass flow controller (MFC), and steps S1 to S7 were performed under reaction conditions shown in Table 2 below to prepare diethylene glycol mono-tertiary-butyl ether (DETB). Other reaction conditions were as follows: production of DETB at 7 atm (step S1); use of a $C_4$ hydrocarbon mixed gas as a lipophilic extractant and use of water as a hydrophilic extractant (step S3); distillation at 1 atm and 100° C. (step S4); distillation under conditions of 3.2 kgf/cm$^2$ and 150° C. (step S5); distillation at 0.1 bar and 210° C. (step S6); and decomposition of diethylene glycol di-tertiary-butyl ether as a byproduct at 3 atm (step S7). In addition, an initial amount of raw materials introduced (DEG+a $C_4$ hydrocarbon compound containing IB) was 1000 g, and a cycling ratio of the reactants (i.e., an amount ratio (weight ratio) of the non-recycled portion of the reaction mixture 11 to the recycled portion of the reaction mixture 11) was 1:10. The amounts of the obtained IB and DEG, the amounts of unreacted byproduct, and total yields of DETB were measured, and measurement results are shown in Table 2 below.

TABLE 1

| Component | isobutene | n-butane | 1-butene | Cis-2-butene | Trans-2-butene | isobutane |
|---|---|---|---|---|---|---|
| Amount (wt %) | 47.6 | 10.9 | 24.7 | 4.6 | 9.3 | 2.9 |

TABLE 2

| | DEG/IB molar ratio | Reaction temperature (° C.) | Amount of byproduct added (g) | Decomposition temperature (° C.) | Weight hourly space velocity (WHSV) | IB produced by decomposition (g) | DEG produced by decomposition (g) | Unreacted byproduct (g) | Total yield of DETB (g) |
|---|---|---|---|---|---|---|---|---|---|
| Example 1 | 2 | 40 | 150 | 130 | 5 | 73.2 | 69.3 | 8.0 | 770 |
| Example 2 | 2 | 50 | 215 | 130 | 5 | 105.6 | 99.9 | 10.4 | 842 |
| Example 3 | 2 | 60 | 253 | 130 | 5 | 123.8 | 117.2 | 11.9 | 831 |
| Example 4 | 1 | 50 | 312 | 130 | 5 | 152.2 | 144.0 | 15.6 | 782 |
| Example 5 | 3 | 50 | 111 | 130 | 5 | 54.3 | 51.4 | 5.6 | 714 |
| Example 6 | 2 | 50 | 212 | 130 | 3 | 107.7 | 101.9 | 1.9 | 850 |
| Example 7 | 2 | 50 | 213 | 130 | 20 | 71.7 | 67.8 | 74.1 | 774 |
| Example 8 | 2 | 50 | 215 | 60 | 5 | 39.9 | 37.8 | 138.1 | 646 |
| Comparative Example 1 | 2 | 40 | — | — | — | — | — | 153 | 513 |
| Comparative Example 2 | 2 | 50 | — | — | — | — | — | 217 | 545 |
| Comparative Example 3 | 2 | 60 | — | — | — | — | — | 258 | 561 |

From the results shown in Table 2 above, it can be confirmed that, when the decomposition reaction temperature in step S7 was 130° C. and the WHSV was 5 (Examples 1 to 5), the byproduct had a decomposition rate of approximately 95%, and the byproduct had a decomposition rate of approximately 99% when the decomposition reaction temperature was 130° C. and the WHSV was 3 (Example 6). In addition, it can be confirmed that the amount of the produced DETB in Examples 1 to 8 including the byproduct decomposition and cycling step (step S7) was at least about 60% greater than the amount thereof in Comparative Examples 1 to 3 in which the byproduct was not reused as a raw material after decomposition.

From the results, it can be confirmed that the preparation method of the glycol mono-tertiary-butyl ether compound according to the present invention includes a product (reaction mixture) recycling step and thus mixing of reactants that do not readily mix is accelerated. In addition, through the product recycling step, a byproduct is decomposed and the obtained products are recycled as reactants, and thus, loss due to the byproduct may be prevented and yield of a desired product may be maximized.

INDUSTRIAL APPLICABILITY

A method of preparing a glycol mono-tertiary-butyl ether compound, according to the present invention, is effectively used to prepare a glycol mono-tertiary-butyl ether compound using a $C_4$ hydrocarbon mixture containing isobutene and a glycol compound as reactants.

The invention claimed is:
1. A method of preparing a glycol mono-tertiary-butyl ether compound, the method comprising:
   a catalytic reaction step for preparing a glycol mono-tertiary-butyl ether compound and a glycol di-tertiary-butyl ether compound as a byproduct by reaction between a glycol compound and a $C_4$ hydrocarbon mixture containing isobutene in the presence of an acidic catalyst;
   a byproduct extraction step for separating the glycol mono-tertiary-butyl ether compound and the glycol di-tertiary-butyl ether compound, prepared in the catalytic reaction step, using a hydrophilic extractant and a lipophilic extractant; and
   a byproduct decomposition and recycling step for decomposing the separated glycol di-tertiary-butyl ether compound into a glycol compound and isobutene and recycling the decomposed glycol compound and isobutene as the reactants to the catalytic reaction step.
2. The method according to claim 1, wherein a decomposition reaction temperature of the byproduct decomposition and recycling step is between 40° C. and 250° C.
3. The method according to claim 1, further comprising a recycling step for partially recycling the reaction mixture (reaction products and unreacted reactants) of the catalytic reaction step, followed by repeating the catalytic reaction step, wherein an amount of a recycled portion of the reaction mixture is 1 to 20 times (weight ratio) that of a non-recycled portion of the reaction mixture.
4. The method according to claim 1, wherein the glycol compound is a compound represented by Formula 1 below, the glycol mono-tertiary-butyl ether compound is a compound represented by Formula 2 below, and the glycol di-tertiary-butyl ether compound is a compound represented by Formula 3 below.

<Formula 1>

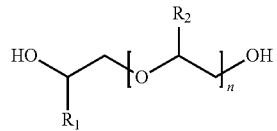

<Formula 2>

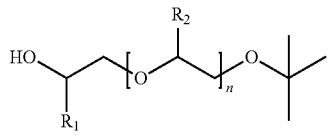

<Formula 3>

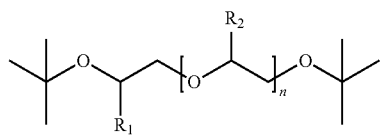

wherein $R_1$ and $R_2$ are each independently a hydrogen atom or a $C_1$-$C_5$ alkyl group, and n is an integer of 0 to 4.

5. The method according to claim 1, wherein an amount of isobutene in the $C_4$ hydrocarbon mixture is 10 wt % or more.

6. The method according to claim 1, wherein the glycol compound and isobutene are used in the catalytic reaction step in a molar ratio of 1:1 to 5:1 (glycol compound: isobutene).

* * * * *